US00PP33072P2

(12) United States Plant Patent
Davis

(10) Patent No.: US PP33,072 P2
(45) Date of Patent: May 18, 2021

(54) ***HYDRANGEA* PLANT NAMED 'SNOWCICLE'**

(50) Latin Name: *Hydrangea quercifolia*
Varietal Denomination: Snowcicle

(71) Applicant: Richard Davis, Accomal, VA (US)

(72) Inventor: Richard Davis, Accomal, VA (US)

( * ) Notice: Subject to any disclaimer, the term of this patent is extended or adjusted under 35 U.S.C. 154(b) by 0 days.

(21) Appl. No.: 16/997,124

(22) Filed: Aug. 19, 2020

(51) Int. Cl.
*A01H 5/02* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 6/48; A01H 5/02
See application file for complete search history.

*Primary Examiner* — Keith O. Robinson
(74) *Attorney, Agent, or Firm* — Penny J. Aguirre

(57) ABSTRACT

A new cultivar of *Hydrangea quercifolia* plant named 'Snowcicle' that is characterized by its inflorescences with sterile flowers comprised of numerous sepals (double) that open white and mature to a blend of rose-red, off white, and olive green, its large inflorescences that are pendulous but well supported by its upright habit with strong stems, and its fall foliage color that is deep wine and burnt orange in color.

2 Drawing Sheets

Botanical classification: *Hydrangea quercifolia.*
Varietal denomination: 'Snowcicle'.

BACKGROUND OF THE INVENTION

The present invention relates to a new and distinct cultivar of *Hydrangea quercifolia* and will be referred to hereafter by its cultivar name, 'Snowcicle'. 'Snowcicle' represents a new oak leaf *Hydrangea*, a perennial shrub grown for landscape use.

'Snowcicle' derived from an ongoing breeding program by the Inventor in Locustville, Va. 'Snowcicle' arose from open pollination of an unnamed and unpatented proprietary plant of *Hydrangea quercifolia* from the Inventor's breeding program in 2003. The male parent is therefore unknown. 'Snowcicle' was selected a single unique plant from amongst the resulting seedlings in 2008.

Asexual propagation of the new cultivar was first accomplished by stem cuttings by the Inventor in 2008 in Locustville, Va. Asexual propagation by stem cuttings and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Snowcicle' as a unique cultivar of *Hydrangea quercifolia.*

1. 'Snowcicle' exhibits inflorescences with sterile flowers comprised of numerous sepals (double) that open white and mature to a blend of rose-red, off white, and olive green.
2. 'Snowcicle' exhibits large inflorescences that are pendulous but well supported by its upright habit with strong stems.
3. 'Snowcicle' exhibits fall foliage color that is deep wine and burnt orange in color.

The female parent of 'Snowcicle' differs from 'Snowcicle' in having smaller inflorescences with less sterile sepals and a less upright plant habit. 'Snowcicle' can be most compared to *Hydrangea quercifolia* cultivars 'Snow Flake' (Not patented) and 'Snow Queen' (U.S. Plant Pat. No. 4,458). Both are similar to 'Snowcicle' in having sterile flowers with sepals that change to pink as they mature. 'Snow Flake' differs from 'Snowcicle' in having inflorescences that are held upright and sterile sepals that change to paler pink in color, 'Snow Queen' differs from 'Snowcicle' in having inflorescences that are held upright and sterile flowers that are single.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant less than one year prior to the effective filing date would have been obtained from a direct or indirect disclosure from the Inventor under 35 U.S.C. 102(b)(1). Disclosures include but may not be limited to website listings by Wayside Gardens, Jackson and Perkins, Spring Hill Nursery, Fast Growing Trees, Michigan Bulb Company, Park Seed, Wilson Bros Gardens, Brighter Blooms, Pleasant Run Nursery, and by Plants Nouveau; the Inventor's representative with a new introduction listing without sales in Nursery Management magazine.

BRIEF DESCRIPTION OF THE DRAWINGS

The accompanying colored photographs illustrate the overall appearance and distinct characteristics of the new *Hydrangea*. The photographs were taken of a plant six years in age as grown outdoors in a garden in Locustville, Va.

The photograph in FIG. 1 provides a view of the plant habit of 'Snowcicle' when inflorescences are fully open.

Figure 1:
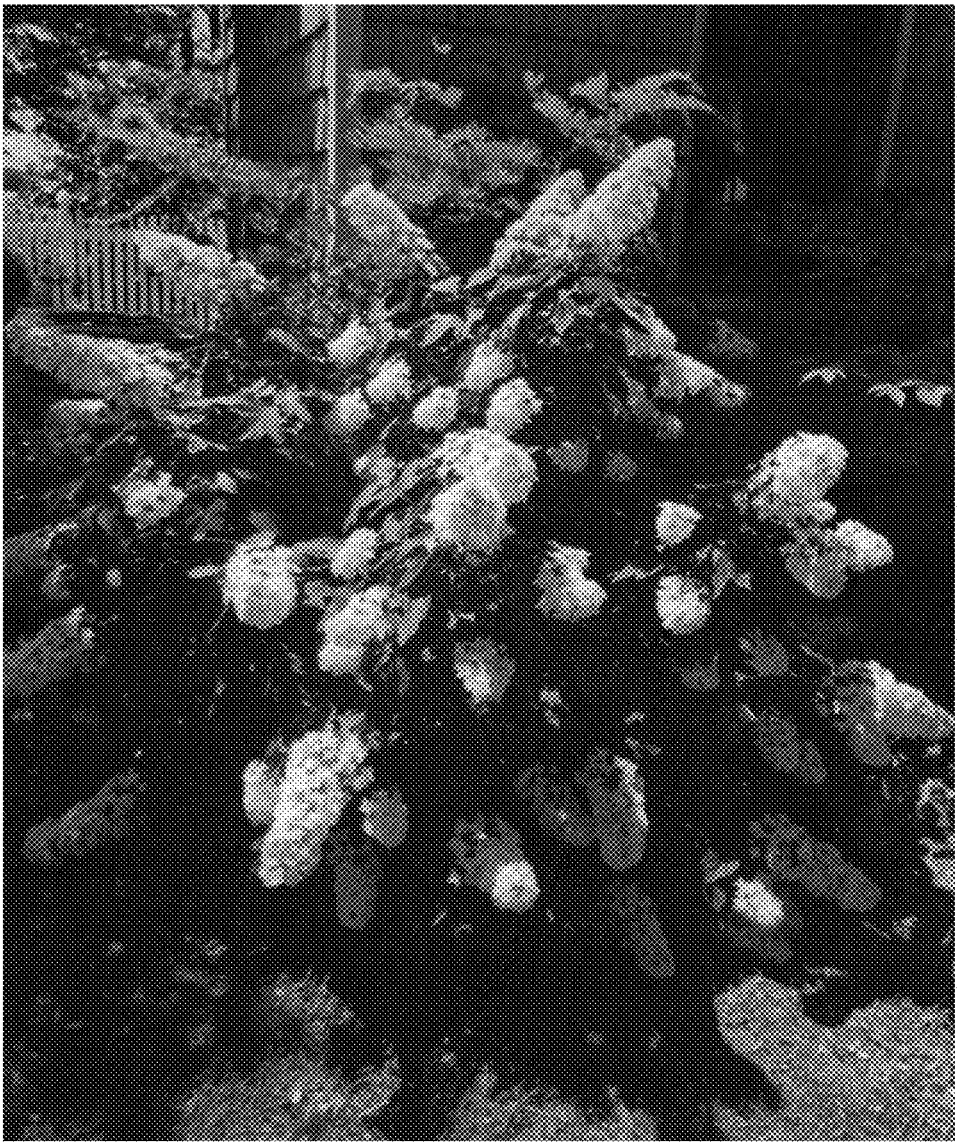
Figure 2:
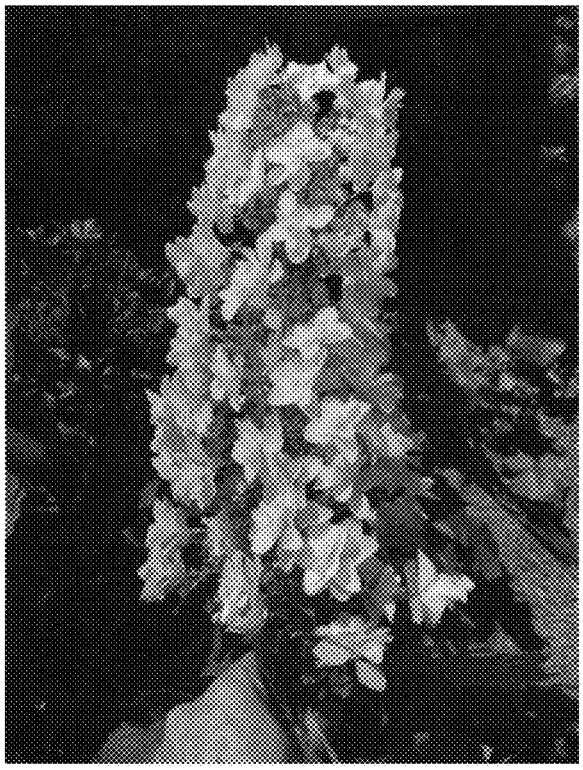

The photograph in FIG. 2 provides a close-up view of a fully open inflorescence of 'Snowcicle'.

Figure 3:
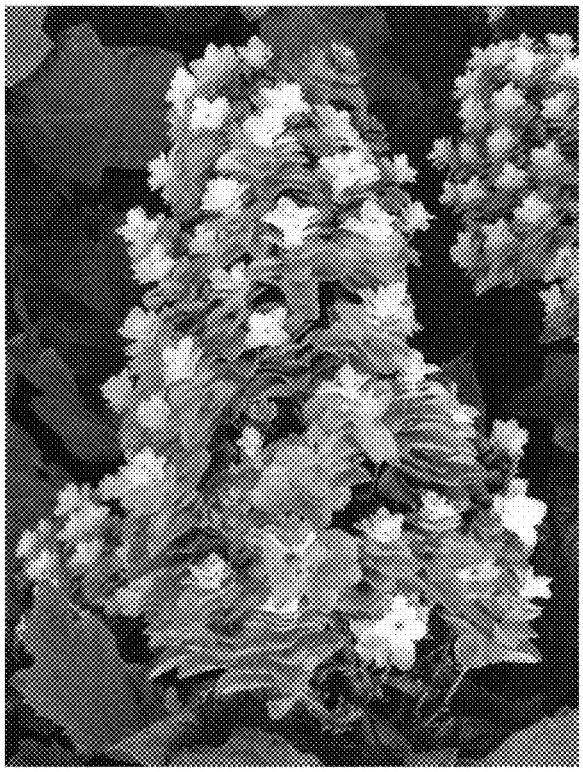

The photograph in FIG. 3 provides a close-up view of an aging inflorescence of 'Snowcicle'.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of plants two years in age as grown outdoors in 2-gallon containers in Mobile, Ala. The phenotype of the new cultivar may vary with variations in environmental, climatic, and cultural conditions, as it has not been tested under all possible environmental conditions. The color determination is in accordance with The 2015 R.H.S. Colour Chart of The Royal Horticultural Society, London, England, except where general color terms of ordinary dictionary significance are used.

General description:

*Blooming period*.—Buds appear in late spring with flowers showy from summer into fall.

*Plant type*.—Perennial flowering shrub.

*Plant habit*.—Sturdy stems, upright.

*Height and spread*.—Reaches up to 2.5 m in height and spread as a mature plant in the landscape.

*Hardiness*.—At least in U.S.D.A. Zones 6 to 9.

*Diseases and pests.*.—No susceptibility and resistance to pests and diseases has been observed.

*Root description*.—Fibrous, primarily N155D and 16D.

*Time required for root development*.—2 to 4 weeks for root initiation with a flowering plant finished in one to two years.

*Growth rate*.—Vigorous for a double flowered *Hydrangea quercifolia*.

Stem description:

*Stem shape*.—Rounded, slightly oval.

*Stem color*.—New growth; 144C with dense pubescence 155A, mature stems; 144B with dense pubescence 165B, bark; 144B and flushed 164A, bark; 166A and 166C in color.

*Stem size*.—Lateral branches an average of 25 cm in length and 7 mm in diameter, main stem 1.4 cm in diameter.

*Stem surface*.—Densely pubescent, bark; medium barked.

*Stem aspect*.—Average angle 60° to 90° (soil level=0°).

*Internode length*.—1 to 7 cm.

*Branching*.—Average of 4 lateral branches from main stem.

*Stem strength*.—Strong.

Foliage description:

*Leaf shape*.—Oak-leaf, ovate to slightly oblong in overall form.

*Leaf division*.—Simple.

*Leaf size*.—Up to 15 cm in length and 13 cm in width.

*Leaf base*.—Obtuse with very base short cuneate.

*Leaf apex*.—Acute with apex of lobes acute.

*Leaf venation*.—Pinnate, upper surface slightly recessed, 146B in color, and slightly hairy with hairs about 2 mm in length and 158A in color, lower leaves raised, 146C in color and moderately covered with hairs about 2.5 mm in length and 158A in color.

*Leaf margins*.—5-lobed with lobes serrate with very tip of serrations mucronate, lobes are moderately deeply lobed with sinuses on mature leaves an average of 2.3 cm in depth.

*Leaf attachment*.—Petiolate.

*Leaf arrangement*.—Opposite.

*Leaf surface*.—New growth upper and lower surface; heavily covered with dense woolly pubescence 155B in color, maturing leaves upper surface; moderately rugose with sparse hairs 155A in color, maturing leaves lower surface; heavily covered with woolly pubescence 155A in color, mature growth upper surface; satiny with sparse fine hairs 155B in color, lower surface; dull with very short matted hairs 194A in color.

*Leaf color*.—Immature leaves upper surface; 146D with dense pubescence 155B, immature leaves lower surface; 157A with very dense pubescence 155A, mature leaves upper surface; a color between 137A and 138A, mature leaves lower surface; 147A and covered with pubescence 194A. color in fall upper and lower surfaces; a blend of 175A, 173A and 147C.

*Petioles*.—An average of 4.5 cm in length and 3.5 mm in diameter, upper surface; flat to slightly channeled, 146D in color, densely covered with pubescence 164C in color, lower surface; 146D in color, with sparse pubescence 164C in color, moderate in strength, held at about a 45° angle and slightly pendulant.

Inflorescence description:

*Inflorescence type*.—Terminal panicle, comprised of double sterile flowers over fertile flowers.

*Lastingness of inflorescence*.—Up to 10 weeks.

*Inflorescence number*.—One per stem.

*Inflorescence size*.—Average of 33 cm in height and 14 cm in diameter.

*Inflorescence bracts*.—An average of 2, up to 2.1 cm in length and 2 mm in width, elliptic in shape, apex acute, base cuneate, margin entire to slightly serrate, surfaces matte, 143A and 145A in color.

*Flower fragrance*.—Very faint sweet fragrance.

*Flower buds*.—Sterile flowers; an average of 1 mm in length and diameter, oval to round in shape, 144A in color, glabrous and matte surface, fertile flowers; an average of 1 mm in length and 1.2 mm in diameter, ovate in shape, 144B in color, glabrous and matte surface.

*Sterile flowers*.—Average of 100 per inflorescence, rotate, held outward, 1.5 cm in depth, 3.5 cm in diameter.

*Fertile flowers*.—An average of 600 per inflorescence, closed campanulate in shape, held at all angles, 3 mm in length, 2 mm in diameter.

*Peduncles*.—Strong, average of 30 cm in length and 4 mm in width, 145B in color, surface is covered with dense short hairs; 0.5 mm in length, match color surface.

*Pedicels*.—Average of 4 cm in length, 1.5 mm in diameter, moderately strong, 145B in color, surface is covered with dense short hairs; 0.5 mm in length, match color surface.

*Petals*.—Sterile flowers; 4, whorl arrangement, ovate to irregular in shape, entire to undulate margins, acute to bluntly acute apex, acute base, up to 5 mm in length, 3 mm in width, upper and lower surface glabrous, color; upper and lower surface color 144D, fertile flowers; 4, rotate in arrangement, triangular in shape, an average of 1 mm in length and width, acute apex, truncate base, entire margins, upper and lower surface glabrous, upper and lower surface color NN155A in color, shed quickly.

*Sepals*.—Sterile flowers; average of 14, rotate in arrangement, broadly ovate-orbicular in shape, entire to undulate margins, broadly acute to rounded apex, acute base, up to 1.5 cm in length and 1.2 cm in width, upper and lower surface glabrous and satiny, color; upper and lower surface when opening; 150D, flushed with 150B, upper and lower surface when fully open; NN155A, center sepals 144A, color when maturing upper and lower surface; a blend of 76A, 145B, and 157C, fertile flowers; 4, rotate in arrangement, elliptic in shape, acute apex, cuneate base, entire margin, an average of 3 mm in length and 2 mm in width, both surfaces glabrous and matte, upper and lower surface 144A in color.

Reproductive organs:

*Stamens*.—Sterile flowers; non-observed, fertile flowers; about 6, filament is 2.5 mm in length and NN155D in color, anther is orbicular in shape, 0.5 mm in length and 149C in color, pollen is very low in quantity and too minimal for color reading.

*Pistils*.—Sterile flowers and fertile flowers; 2, style is an average of 1.5 mm in length and 157D in color, stigma is 0.5 mm in diameter and 155A in color, ovary is 157D in color.

*Fruit and seed*.—No fruit or seed production has been observed to date.

It is claimed:

1. A new and distinct cultivar of *Hydrangea* plant named 'Snowcicle' substantially as herein illustrated and described.

* * * * *